US012657829B2

(12) United States Patent (10) Patent No.: US 12,657,829 B2

Lutz et al. (45) Date of Patent: Jun. 16, 2026

(54) COMPUTER-IMPLEMENTED METHOD AND ASSOCIATED DEVICE FOR MODELLING A JOINT OF A PATIENT

(71) Applicant: Areas, Grenoble (FR)

(72) Inventors: Christian Lutz, Eschau (FR); Bertrand Sonnery-Cottet, Lyons (FR); Pierre Imbert, Frejus (FR); Yvon Gautier, Grenoble (FR); Romain Benoit, Brié-et-Angonnes (FR)

(73) Assignee: AREAS, Grenoble (FR)

( * ) Notice: Subject to any disclaimer, the term of this patent is extended or adjusted under 35 U.S.C. 154(b) by 0 days.

(21) Appl. No.: 19/331,275

(22) Filed: Sep. 17, 2025

(65) Prior Publication Data

US 2026/0073635 A1 Mar. 12, 2026

Related U.S. Application Data

(63) Continuation of application No. PCT/EP2024/059848, filed on Apr. 11, 2024.

(30) Foreign Application Priority Data

Apr. 13, 2023 (FR) ...................................... 2303713

(51) Int. Cl.
*G06T 17/20* (2006.01)
*A61B 34/10* (2016.01)
(Continued)

(52) U.S. Cl.
CPC .............. *G06T 17/20* (2013.01); *A61B 34/10* (2016.02); *G06N 3/092* (2023.01); *G06T 7/579* (2017.01);
(Continued)

(58) Field of Classification Search
CPC ..................... G06T 17/20; G06T 7/579; G06T 2207/10088; A61B 34/10; A61B 2034/105; G06N 3/092
See application file for complete search history.

(56) References Cited

U.S. PATENT DOCUMENTS 7,123,255 B2 10/2006 Trousset et al.
10,499,996 B2 12/2019 de Almeida Barreto
(Continued)

FOREIGN PATENT DOCUMENTS

DE 102020117188 A1 12/2021
EP 3375399 A2 9/2018
(Continued)

OTHER PUBLICATIONS

Banach et al., "Visual Localisation for Knee Arthroscopy", International Journal of Computer Assisted Radiology and Surgery, Springer, DE, vol. 16, No. 12, Jul. 4, 2021 (Jul. 4, 2021), pp. 2137-2145, [retrieved on Jul. 4, 2021], DOI: 10.1007/S11548-021-02444-8, ISSN: 1864-6410, XP037628538.
(Continued)

*Primary Examiner* — Chong Wu
(74) *Attorney, Agent, or Firm* — Perkins Coie LLP

(57) ABSTRACT

The invention relates to a computer-implemented method and an associated device for modelling a joint of a patient for real-time assistance in performing at least one bone tunnel by arthroscopy in said joint, said method comprising: receiving a stream of intraoperative monocular two-dimensional images obtained using an imaging device, each of the intraoperative monocular two-dimensional images being obtained at a time t and comprising at least a region of interest of the joint; for each intraoperative monocular two-dimensional image, calculating a depth map associated with time t by implementing a first previously trained learning model, said first learning model being configured to
(Continued)

receive as input at least said intraoperative monocular two-dimensional image obtained at time t; calculating a current partial three-dimensional model of the patient's joint associated with a current time $t_c$, on the basis of at least one depth map associated with the current time $t_c$, at least one depth map associated with a previous time $t_c-\Delta t$ relative to the current time $t_c$, localization information of the imaging device, and a preoperative three-dimensional model of the patient's joint.

20 Claims, 6 Drawing Sheets

(51) Int. Cl.
    *G06N 3/092*       (2023.01)
    *G06T 7/579*       (2017.01)

(52) U.S. Cl.
    CPC .................. *A61B 2034/105* (2016.02); *G06T 2207/10088* (2013.01)

(56) References Cited

U.S. PATENT DOCUMENTS

| | | | |
|---|---|---|---|
| 11,730,342 | B2 | 8/2023 | Ries et al. |
| 12,064,187 | B2 | 8/2024 | Bleunven et al. |
| 2003/0210812 | A1 | 11/2003 | Khamene et al. |
| 2006/0161052 | A1 | 7/2006 | Columbet et al. |
| 2013/0211232 | A1 | 8/2013 | Murphy et al. |
| 2016/0338776 | A1 | 11/2016 | Jaramaz et al. |
| 2018/0174311 | A1* | 6/2018 | Kluckner ............... G06V 10/25 |
| 2021/0259774 | A1 | 8/2021 | Fouts et al. |
| 2021/0322148 | A1 | 10/2021 | Mitra et al. |
| 2022/0296302 | A1 | 9/2022 | Bleunven et al. |
| 2023/0074630 | A1 | 3/2023 | Knopf |
| 2023/0200928 | A1 | 6/2023 | Quist et al. |
| 2023/0363831 | A1* | 11/2023 | Jaramaz ................... G06N 3/09 |
| 2024/0358224 | A1 | 10/2024 | Quist et al. |
| 2025/0049448 | A1 | 2/2025 | Quist et al. |

FOREIGN PATENT DOCUMENTS

| | | | |
|---|---|---|---|
| EP | 3922204 | A1 | 12/2021 |
| EP | 3936075 | A2 | 1/2022 |
| FR | 2920565 | B1 | 12/2009 |
| WO | 2021257672 | A1 | 12/2021 |
| WO | 2022195303 | A1 | 9/2022 |
| WO | 2024089352 | A1 | 5/2024 |
| WO | 2024213641 | A1 | 10/2024 |
| WO | 2025068248 | A1 | 4/2025 |
| WO | 2025071921 | A1 | 4/2025 |

OTHER PUBLICATIONS

Barratt DC, Penney GP, Chan CS, Slomczykowski M, Carter TJ, Edwards PJ, Hawkes DJ. Self-Calibrating 3D- Ultrasound-Based Bone Registration for Minimally Invasive Orthopedic Surgery, IEEE Transactions On Medical Imaging. Mar. 2006;25(3).

Cabitza F, Locoro A, Banfi G. Machine learning in orthopedics: a literature review. Frontiers in bioengineering and biotechnology. 2018 Jun. 27;6:75.

Chen et al., "SLAM Endoscopy enhanced by adversarial depth prediction", arxiv.org, Cornell University Library, 201 Olin Library Cornell University Ithaca, NY 14853, Jun. 29, 2019 (Jun. 29, 2019), XP081379828.

Cilla M, Borgiani E, Marinez J, Duda GN, Checa S. Machine learning techniques for the optimization of joint replacements: Application to a short-stem hip implant. Plos one. Sep. 5, 2017;12(9):e0183755.

Dhaher YY, Salehghaffari S, Adouni M. Anterior laxity, graft-tunnel interaction and surgical design variations during anterior cruciate ligament reconstruction: A probabilistoc simulation of the surgery. Journal of biomechanics. Sep. 6, 2016;43(13):3009-16.

Kumar et al., "DepthNet: A Recurrent Neural Network Architecture for Monocular Depth Prediction", 2018 IEEE/CVF Conference on Computer Vision and Pattern Recognition Workshops (CVPRW), IEEE, Jun. 18, 2018 (Jun. 18, 2018), pp. 396-404, DOI: 10.1109/ CVPRW.2018.00066, XP033475663.

Musahl V, Plakseychuk A, VanScyoc A, Sasaki T, Debski RE, Mcmahon PJ, Fu FH. Varying femoral tunnels between the anatomical footprint and isometric positions: effect on kinematics of the anterior cruciate ligament-reconstructed knee. The American journal of sports medicine. May 2005;33(5):712-8.

Osti M, Krawinkel A, Ostermann M, Hoffelner T, Benedetto KP, Femoral and tibial graft tunnel parameters after transtibial, anteromedial portal, and outside-in single-bundle anterior cruciate ligament reconstruction. The American journal of sports medicine. Sep. 2015; 43(9):2250-8.

Raposo et al., "Video-based computer navigation in knee arthroscopy for patient-specific ACL reconstruction", International Journal of Computer Assisted Radiology and Surgery, https://doi.org//10. 1007/s11548-019-02021-0, Received: Feb. 7, 2019, Accepted: Jun. 24, 2019, Published online: Jun. 29, 2019, 11 pages.

International Search Report Translation and Written Opinion, I.A. No. PCT/EP2024/059848, ISA/EP, Mail date: Jul. 1, 2024, 9 pages.

File History of related U.S. Appl. No. 63/819,028, filed Jun. 6, 2025.

File History of related U.S. Appl. No. 63/819,052, filed Jun. 6, 2025.

File History of related U.S. Appl. No. 63/839,639, filed Jul. 7, 2025.

File History of related U.S. Appl. No. 63/844,341, filed Jul. 15, 2025.

File History of related U.S. Appl. No. 63/844,973, filed Jul. 16, 2025.

File History and the references cited therein of related U.S. Appl. No. 19/122,814, filed Oct. 23, 2023.

Rodeo SA, Kawamura S, Kim HJ, Dynybil C, Ying L., "Tendon healing in a bone tunnel differs at the tunnel entrance versus the tunnel exit: an effect of graft-tunnel motion", The American Journal of Sports Medicine. Nov. 2006; 34(11): 1790-800.

File History of related U.S. Appl. No. 63/884,097, filed Sep. 18, 2025.

\* cited by examiner

COMPUTER-IMPLEMENTED METHOD AND ASSOCIATED DEVICE FOR MODELLING A JOINT OF A PATIENT

FIELD OF THE INVENTION

The present invention relates to assistance in surgery by arthroscopy. More particularly, the invention relates to a computer-implemented method and an associated device for modelling a joint of a patient. In particular, the method described herein finds its interest in assisting in making bone tunnels in a joint of a patient during an operation.

PRIOR ART

Digital surgical assistance can be useful and beneficial during surgical procedures such as arthroscopic surgery. Indeed, when a surgeon has to operate on a part of the body of an individual, they do not have full visibility of the inside of that part of the body. Thus, the actions of a surgeon could be more precise if they could visualise in real time the positioning of their tools in the vicinity of and inside the part of the body on which they are to operate.

Ligament reconstruction surgeries of the knee are operations that consist in replacing one or more ligaments of the knee joint, connecting the femur to the tibia with a strip of tendinous tissue, which will constitute the neoligament, taken from the patient (autografting) or, more rarely, taken post-mortem from donors (allografting). The surgeon will then produce a bone tunnel in the femur and a bone tunnel in the tibia and position these tunnels in the insertions of the injured ligament, and then pass the graft into these tunnels before securing it.

Some solutions have been developed for clinical research purposes, but none have yet entered routine use in the operating theatre.

The invention falls within this context.

SUMMARY

The invention relates to a computer-implemented method for modelling a joint of a patient for real-time assistance in making at least one bone tunnel by arthroscopy in said joint, comprising:

a step of obtaining, using an imaging device, a stream of monocular intraoperative two-dimensional images, each of the monocular intraoperative two-dimensional images being obtained at a current time $t_c$ and comprising at least a portion of interest of the joint;

a first step of calculating, for each monocular intraoperative two-dimensional image, an associated depth map, by implementing a previously trained learning model;

a second step of calculating a current partial three-dimensional model of the joint of the patient at the current time $t_c$, on the basis of at least one monocular intraoperative two-dimensional image obtained at and/or before the current time $t_c$, at least one depth map calculated at and/or before the current time $t_c$, information relating to a current position and orientation of the imaging device, and a complete preoperative three-dimensional model of the joint of the patient.

Thus, the method makes it possible to guide a healthcare professional during an operation by presenting a model of the anatomy of the patient, enabling them to access a calculated partial three-dimensional model of real images. This template will guide the healthcare professional in the positioning and drilling of bone tunnels. The combination of at least one monocular intraoperative two-dimensional image, at least one associated depth map and information relating to a current position and orientation of the imaging device, associated with a reconstruction algorithm as described in the present application, makes it possible to generate a current partial three-dimensional model of the joint of the patient at a time t.

One of the particularities of the invention is that use is not made of a depth sensor of the Lidar type, or of an RGB-D camera capable of directly acquiring a depth map, or of a stereoscopic acquisition system. The two-dimensional images used here are monocular images. The invention makes it possible to predict the joint depth observed with an imaging device during an operation reliably and accurately, in accordance with the actual geometry of the patient.

Advantageously, the previously trained learning model is an artificial neural network.

Advantageously, the second calculation step is carried out with an algorithm of the SLAM type (in English: "simultaneous localisation and mapping"). The algorithm advantageously uses the monocular intraoperative two-dimensional image stream delivered by the imaging device as well as the depth maps calculated with the previously trained learning model to calculate a real-time three-dimensional model the position and orientation of which relative to the imaging device are known.

Advantageously, the second calculation step is performed using a reinforcement learning model. Such a method makes it possible to quickly obtain an accurate partial three-dimensional model.

Advantageously, the learning model was previously trained with a set of monocular intraoperative two-dimensional training images and a set of associated ground truths, said ground truths being distances, being distances between a virtual imaging device and at least one object included in the set of monocular intraoperative two-dimensional training images and said training images being associated with virtual images derived from a preoperative three-dimensional model of the joint of the patient. There is, to the knowledge of the inventors, no training database composed of images similar to arthroscopic images. Thus, the learning model is specifically trained on images close to the intraoperative images, and is thus more precise.

Advantageously, the preoperative three-dimensional model was obtained from two-dimensional medical images.

Advantageously, the learning model was previously trained with a set of monocular intraoperative two-dimensional training images and a set of associated ground truths, said ground truths being distances obtained using pairs of images acquired at different times using an imaging device called a training imaging device and information relating to positions and orientations of said training imaging device. Thus, the learning model is specifically trained on images close to the intraoperative images, and is thus more precise.

It is possible to sequence the training phases of the model with training data sets that are very close in content and quality to the data that the model will process, and thus increase the accuracy of the model.

Advantageously, the learning model was previously trained with a set of monocular intraoperative two-dimensional training images and a set of associated ground truths, said ground truths being distances measured on cadaveric joints, and said training images being two-dimensional images of said cadaveric joints. Thus, the learning model is specifically trained on images close to the intraoperative images, and is thus more precise.

Advantageously, the method comprises, between the first calculation step and the second calculation step, an intermediate step of filtering outlier data in each calculated depth map. This step improves the accuracy of the calculation of the current partial three-dimensional model.

Another aspect of the invention relates to a computer device comprising a circuit configured to implement a method as described above.

Another aspect of the invention relates to a computer program product including instructions for implementing steps of the method described above.

Still another aspect of the invention relates to a non-transient computer-readable recording medium comprising instructions which, when executed by a computer, lead the latter to implement steps of the method described above.

Another way of describing the invention is set forth below:

The invention relates to a computer-implemented method for modelling a joint of a patient for real-time assistance in making at least one bone tunnel by arthroscopy in said joint, comprising:

receiving a stream of monocular intraoperative two-dimensional images obtained using an imaging device, each of the monocular intraoperative two-dimensional images being obtained at a time t and comprising at least a portion of interest of the joint;

for each monocular intraoperative two-dimensional image, calculating a depth map associated with the time t, by implementing a first previously trained learning model, said first learning model being configured to receive as input at least said monocular intraoperative two-dimensional image obtained at the time t;

calculating a current partial three-dimensional model of the joint of the patient associated with a current time $t_c$, based on at least one depth map associated with the current time $t_c$ and at least one depth map associated with a previous time $(t_c-\Delta t)$ at the current time $t_c$, location information of the imaging device, and a preoperative three-dimensional model of the joint of the patient.

In an embodiment, said location information of the imaging device comprises at least:

measured location information comprising: a first position and orientation of the imaging device and a second position and orientation of the imaging device, being measured by a tracking device respectively at said current time $t_c$ and at said previous time $(t_c-\Delta t)$; and calculated location information comprising: a first position and orientation of the imaging device calculated on the basis of at least one monocular intraoperative two-dimensional image associated with said current time $t_c$ and a second position and orientation of the imaging device calculated on the basis of at least one monocular intraoperative two-dimensional image associated with said previous time $(t_c-\Delta t)$.

In an embodiment, said calculated location information is obtained by an algorithm of the "Structure from motion-"type.

In an embodiment, the computer-implemented method for modelling a joint of a patient further comprises, before calculating said current partial three-dimensional model of the joint of the patient associated with a current time $t_c$, obtaining a prediction of a mesh associated with the current time $t_c$, said mesh being representative of at least a portion of interest of the joint, using a second trained model configured to receive as input a depth map associated with said current time $t_c$ and a depth map associated with said previous time $(t_c-\Delta t)$.

In an embodiment, calculating a current partial three-dimensional model is performed by a graphical neural network receiving as input said measured location information, said calculated location information, said prediction of a mesh and said preoperative three-dimensional model of the joint of the patient.

In an embodiment, calculating a partial three-dimensional of the joint of the patient is performed by a reinforcement learning model being configured to receive as input said measured location information, said calculated location information, said prediction of a mesh and said preoperative three-dimensional model of the joint of the patient.

In an embodiment, the first previously trained learning model is an artificial neural network.

In an embodiment, the first learning model was previously trained with a first set of monocular intraoperative two-dimensional training images and a set of associated ground truths, said ground truths being distances between a virtual imaging device and at least one object included in the set of monocular intraoperative two-dimensional training images, each of the training images representing a virtual image obtained with said virtual imaging device comprising in its field of view said at least one object, the object being the preoperative three-dimensional model of the joint of the patient.

In one embodiment, the preoperative three-dimensional model was obtained from two-dimensional medical images, said two-dimensional medical images comprising at least said portion of interest of the joint.

In one embodiment, said preoperative three-dimensional model of the joint of the patient is obtained from images acquired by "Magnetic Resonance Imaging", said acquired images comprising at least said portion of interest of the joint.

In an embodiment, the first learning model was previously trained with a second set of monocular intraoperative two-dimensional training images and a set of associated ground truths, said ground truths being distances obtained using pairs of images acquired at different times using an imaging device, said training imaging device, and information relating to positions and orientations of said training imaging device.

In an embodiment, the first learning model was previously trained with a third training set comprising a plurality of training subsets acquired on a plurality of cadavers by said training imaging device, each training subset comprising:

a monocular two-dimensional image, comprising at least a portion of interest of the cadaveric joint; and the associated ground truth, said associated ground truth being a depth map representative of the distance between the training imaging device and said at least one portion of interest of the cadaveric joint represented in the monocular two-dimensional image.

In an embodiment, the computer-implemented method for modelling a joint of a patient further comprises, prior to obtaining the mesh prediction, an intermediate step of filtering outlier data from the depth map associated with said current time $t_c$ and the depth map associated with said previous time $(t_c-\Delta t)$ by comparing said depth maps.

Another aspect of the invention relates to a device for modelling a joint of a patient for real-time assistance in making at least one bone tunnel by arthroscopy in said joint, said device comprising:

at least one input configured to receive a stream of monocular intraoperative two-dimensional images obtained using an imaging device, each of the monocular intraoperative two-dimensional images being obtained at a time t and comprising at least a portion of interest of the joint;

at least one processor configured to:

for each monocular intraoperative two-dimensional image, calculate a depth map associated with the time t, by implementing a first previously trained learning model, said first learning model being configured to receive as input at least said monocular intraoperative two-dimensional image obtained at the time t;

calculate a current partial three-dimensional model of the joint of the patient associated with a current time $t_c$, on the basis of at least one depth map associated with the current time $t_c$ and of at least one depth map associated with a previous time $(t_c-\Delta t)$ at the current time $t_c$, of location information of the imaging device, and of a preoperative three-dimensional model of the joint of the patient.

at least one output configured to provide said current partial three-dimensional model of the joint of the patient associated with a current time $t_c$.

Another aspect of the invention relates to a computer program product including instructions for implementing steps of the method according to any one of the embodiments, when this program is executed by a processor.

Another aspect of the invention relates to a computer-readable recording medium comprising instructions which, when they are executed by a computer, cause it to implement the method according to any one of the embodiments.

DEFINITIONS

The term "processor" should not be interpreted as being limited to hardware capable of running software, and generally refers to a processing device, which may, for example, comprise a computer, a microprocessor, an integrated circuit or a programmable logic device (PLD). The processor may also comprise one or more graphics processing units (GPUs), whether used for computer graphics and image processing or other functions. Furthermore, the instructions and/or data enabling the execution of the associated and/or resulting functionalities may be stored on any medium readable by the processor such as, for example, an integrated circuit, a hard disk, a CD (Compact Disc), an optical disk such as a DVD (Digital Versatile Disc), a RAM (Random-Access Memory) or a ROM (Read-Only Memory). Instructions may be stored in particular in hardware, software, firmware or any combination thereof.

DETAILED DESCRIPTION

Figure 2:
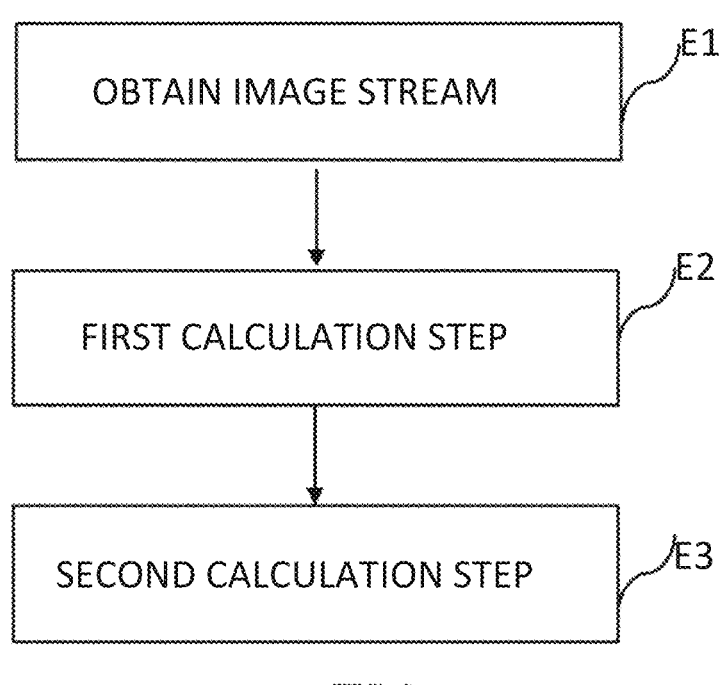
FIG. 2 shows a flowchart of an example of steps for implementing a method for modelling a joint of a patient.
Figure 5:
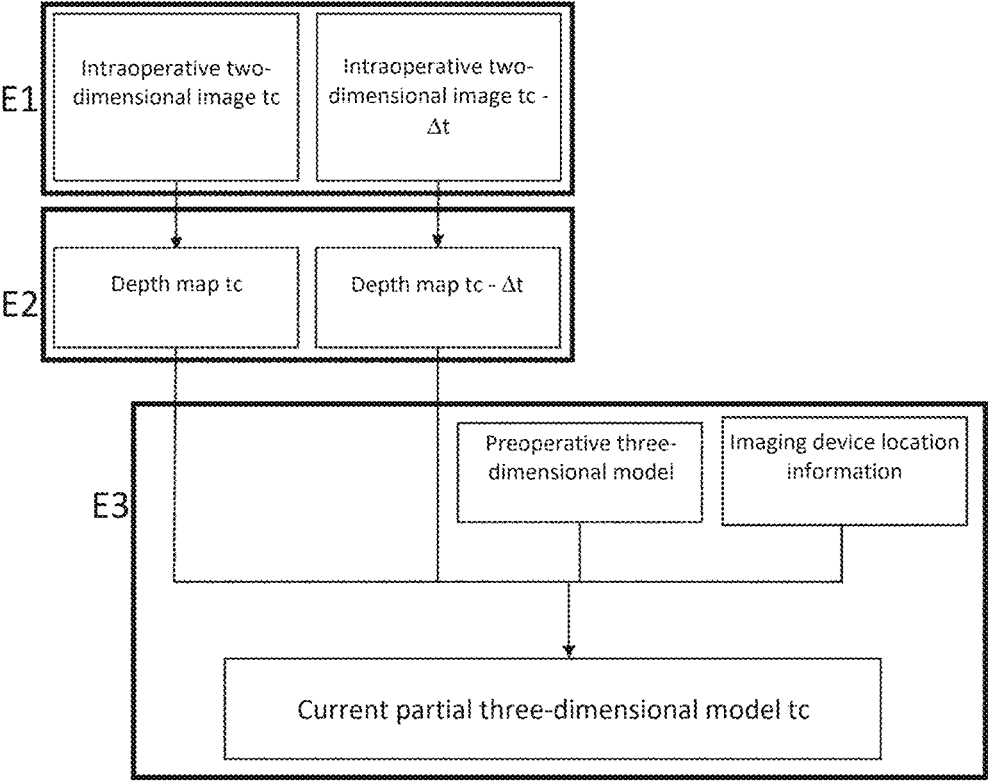
FIG. 5 is a block diagram that illustrates in detail the steps of the method for modelling a joint of a patient according to one or more embodiments.

The present invention relates to a computer-implemented method 100, illustrated in FIG. 2, for modelling a joint of a patient. In addition, FIG. 5 shows a block diagram that illustrates in more detail the contents of steps E1, E2 and E3 of the computer-implemented method 100 for modelling a joint of a patient for real-time assistance in making at least one bone tunnel by arthroscopy in said joint according to one or more embodiments.

In the present description, the joint chosen as an illustrative example is one of the knees of the patient. Indeed, the present method 100 could also be applied during surgery of a shoulder, ankle, elbow, hip or wrist.

As an example, the situation here is that the patient must undergo a surgical procedure, by arthroscopy, for ligament reconstruction of their knee.

The method 100 makes it possible to obtain by calculation a three-dimensional intraoperative model of the joint (i.e. a current partial three-dimensional model of the joint of the patient), which can be made visible to the manipulator (e.g., surgeon, physician) during the surgical operation. With this intraoperative three-dimensional model, it is possible to guide the manipulator/surgeon performing the surgery, for example when making bone tunnels.

Figure 1:
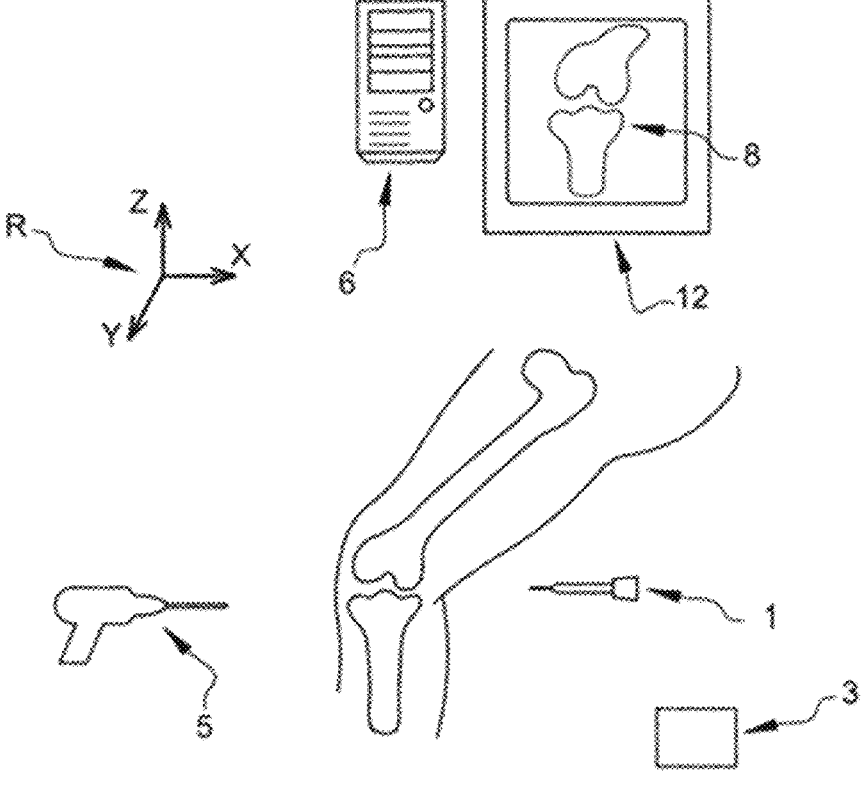
FIG. 1 shows a plurality of elements used when performing a computer-implemented method to model a joint of a patient according to one or more embodiments.

FIG. 1 illustrates a plurality of elements used in one or more embodiments of the invention.

During arthroscopic surgery on the joint of the patient, an imaging device 1 acquires a stream, preferably continuous, of monocular intraoperative two-dimensional images, each of the monocular intraoperative two-dimensional images being obtained at a time t and comprising at least a portion of interest of the joint. In one example, monocular intraoperative two-dimensional images comprise the entire joint of the patient.

For example, the imaging device 1 is an arthroscope. An arthroscope is a thin tube equipped with a miniaturised lens connected to a camera allowing to visualize the interior of a joint. The arthroscope is inserted into the joint after incision thereof. The diameter of the arthroscope is of the order of a few millimetres.

Furthermore, during an operation by arthroscopy to produce one or more bone tunnels, a surgeon can use a surgical piercing instrument 5 such as a surgical motor or surgical drill, comprising a piercing end. The piercing end makes it possible to produce tunnels in the bone structures.

During the surgery, a monitoring device 3 dedicated to monitoring different elements used during the intervention is used. The monitoring device 3 comprises for example one or more cameras making it possible to locate and track in real time the position in space of the various instruments used during the operation, such as the imaging device 1 and the surgical piercing instrument 5. The monitoring device 3 may further comprise one or more motion sensors.

On the imaging device 1 and the surgical piercing instrument 5 are fixed one or more markers configured to emit, receive or reflect a signal (e.g. electromagnetic radiation, infrared radiation) so as to be located by the monitoring device 3. One or more passive markers can be secured and the imaging device 1 and the surgical piercing instrument 5, so as to be visible on images acquired by the monitoring device. For example, the passive markers are QR codes, AR tags or 3D markers.

The position in space of the imaging device 1 and of the piercing instrument 5 with respect to the monitoring device 3 can then be known by triangulation.

If the geometry of each monitored instrument such as the imaging device 1 and the piercing instrument 5 is known, the monitoring device 3 directly recognises these without equipping them with markers and their respective position and orientation with respect to the monitoring device is known.

For example, the monitoring device 3 is a system of the Hololens™ type making it possible to locate, using cameras, among other things, the imaging device 1 and the surgical piercing instrument 5 in an operating theatre. Thus, as soon as the imaging device 1 or the surgical piercing instrument 5 are in the field of vision of the cameras, this or these are located and their positions are calculated and recorded.

For example, still during the operation, the programmable device 6 receives in real time a signal coming from the monitoring device 3, on the basis of which it calculates the position and the orientation in real time of the imaging device 2 with respect to the a fixed reference frame R. The position and the orientation of the imaging device 2 comprise for example three coordinates and three angles.

Also, still during the operation, the programmable device 6 receives in real time a signal coming from the monitoring device 3, on the basis of which it calculates the position and the orientation in real time of the piercing end of the surgical piercing instrument 5. The position and orientation of the piercing end of the surgical piercing instrument 5 comprise for example three coordinates and three angles.

As will be explained, the method 100 can use the two-dimensional image stream acquired by the imaging device 1 during the operation.

FIGS. 2 and 5 are example flowcharts representing steps of a method for modelling a joint of a patient according to one or more embodiments.

In a step E1, a stream of monocular intraoperative two-dimensional images from the imaging device 1 is obtained in real time. The monocular intraoperative two-dimensional images comprising a portion of interest of the joint.

The step E1 comprises receiving a stream of monocular intraoperative two-dimensional images obtained using the imaging device 1, each of the monocular intraoperative two-dimensional images being obtained at a time t and comprising at least a portion of interest of the joint. Annotating each image with the acquisition time t makes it possible to locate in time the order of the monocular intraoperative two-dimensional images in the image stream. For example, the time t can be any time among N times: $t_1$, $t_2$, ... $t_N$, the time $t_N$ being the time of acquisition of the last monocular intraoperative two-dimensional image of the image stream. The time $t_N$ is referred to as the current time $t_c$.

Optionally, the monocular intraoperative two-dimensional image stream is pre-processed before a first calculation step E2. In the case where the imaging device is an arthroscope, it conventionally has several video stream qualities (HD, Full-HD, 4K, 8K) rated at 60 Hz. The optional pre-processing of the monocular intraoperative two-dimensional image stream then consists in resizing the latter as an HD stream so as to adapt the resolution of the stream to the learning model used. In addition, temporal subsampling of the images can be performed in order to enable processing of the video stream in real time. For example, sampling between one in 3 images and one in 10 images may be used.

During the first calculation step E2, for each monocular intraoperative two-dimensional image obtained at a current time $t_c$, a depth map associated with the monocular intraoperative two-dimensional image (i.e. depth map associated with the time $t_c$) is calculated, by implementing a first previously trained learning model. Depth map associated with an image comprising a plurality of pixels, means an image comprising the same number of pixels as the plurality of pixels, wherein each pixel has as value the distance of the object contained in the corresponding pixel in the image associated with the imaging device.

In a second calculation step E3, a current partial three-dimensional model 8 of the joint of the patient at time t is calculated. The calculation uses at least one monocular intraoperative two-dimensional image obtained at and/or before the current time $t_c$, at least one depth map calculated at and/or before the time (i.e., at least one depth map associated with the current time $t_c$ and at least one depth map associated with a preceding time ($t_c$–$\Delta$t)), information relating to a current position and orientation of the imaging device 1 (i.e., location information on the imaging device 1), and a complete preoperative three-dimensional model of the joint of the patient.

Once the current partial three-dimensional model 8 has been calculated, it can be displayed on a display device 12 and viewed by the healthcare professional performing the surgical operation.

The first calculation step E2 will now be described in more detail.

It should be noted that the images of joints captured using an arthroscope have the particularity of presenting few characteristic points that can facilitate the operation of learning models such as artificial neural networks. Training an artificial neural network so that it produces a depth map associated with an arthroscopic image can be difficult if the choice of training data is not adequate. Arthroscopic images may in fact be blurry, overexposed, have limited texture, or have obstructions. Furthermore, the imaging distances when navigating an arthroscope can vary over large value ranges. All of these conditions make training a learning model very difficult.

One of the advantages of the invention lies in the use of training data that are very close in content and quality to the data processed by the learning model, which will make it possible to make the learning model more accurate after training when it calculates depth maps. The accuracy of the depth maps is important because the depth maps will be used in combination with the monocular intraoperative two-dimensional images to calculate the partial three-dimensional model at each current time $t_c$.

In one or more embodiments, the first previously trained learning model used to compute the depth maps associated with the monocular intraoperative two-dimensional images is an artificial neural network. In other words, step E2 comprises calculating a depth map associated with the time t for each monocular intraoperative two-dimensional image obtained. The calculation of each depth map can be carried out by implementing a first previously trained learning model. This first learning model can be configured to receive as input at least one of the monocular intraoperative two-dimensional images obtained at a time t and provide as output a depth map associated with the input image (i.e., a depth map associated with the time t).

The first previously trained learning model may be a neural network of the MiDaS, DepthNet, ResNet, UNet, Pix2Depth, GAN or CNN type. Regardless of the neural network used, the depth map associated with the time t can be calculated from said monocular intraoperative two-dimensional image obtained at the time t. For example, an artificial neural network with a monodepth2 architecture, or of the Unet, PyDNet, DSNet, FastDepth, DeepMatch VO, Ganvo or MiDas type can be used.

In an alternative embodiment, the first learning model may be configured to receive as input two of the monocular intraoperative two-dimensional images obtained at two distinct times (i.e., separated by an interval Δt).

Consequently, several depth maps associated with successive times are generated.

Using a triangulation algorithm (i.e., a "multiview stereo" algorithm), and based on at least two calculated depth maps, it is possible to obtain a calculated distance. This calculated distance may be: a distance between the imaging device 1 and an object included in the monocular intraoperative two-dimensional image, a distance between a virtual imaging device and an object included in the monocular intraoperative two-dimensional image, or a distance between a training imaging device and an object included in the monocular intraoperative two-dimensional image. The object included in the monocular intraoperative two-dimensional image may be all or part of the joint of the patient. A distance can be calculated for each pixel of the monocular intraoperative two-dimensional image. In another example, a distance is associated with a set of pixels.

As part of the image analysis used during training of the first learning model, the object included in the monocular intraoperative two-dimensional image may be a preoperative three-dimensional model of the joint of the patient or a model of cadaveric joints. In these cases, the calculated distance values are compared with the previously measured distance values. The measured distance values can therefore be obtained on a cadaveric joint model, an artificial joint model, or on any type of model representative of the anatomy of the joint in question.

Figure 3:
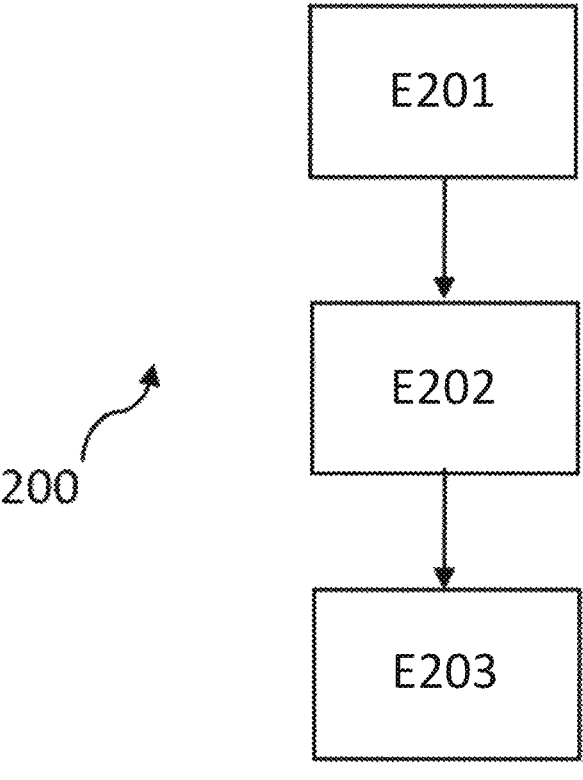
FIG. 3 shows a flowchart of an example sequence of steps for training a learning model used to calculate depth maps.

Prior to the implementation of the method 100, the first learning model, for example an artificial neural network, will be trained from training data, during a training phase 200 illustrated in FIG. 3.

In an embodiment, the first learning model is pretrained with a first set of monocular intraoperative two-dimensional training images and a set of associated ground truths, the ground truths being distances between a virtual imaging device and at least one object included in the set of monocular intraoperative two-dimensional training images, each of the training images representing a virtual image obtained with the virtual imaging device comprising in its field of view said at least one object, the object being the preoperative three-dimensional model of the joint of the patient.

In one embodiment, the preoperative three-dimensional model is obtained from two-dimensional medical images, the two-dimensional medical images comprising at least the portion of interest of the joint. The preoperative three-dimensional model can be obtained by a convolutional neural network or CNN (e.g., three-dimensional CNN) or by a 3D reconstruction algorithm based on image processing approaches such as segmentation and reconstruction.

In one embodiment, the preoperative three-dimensional model of the joint of the patient is obtained from images acquired by "Magnetic Resonance Imaging" (MRI), the acquired images comprising at least the portion of interest of the joint. Obtaining the preoperative three-dimensional model of the joint from MRI images provides a detailed view of the joint anatomy, facilitating the distinction of different anatomical structures including bones, ligaments, tendons and soft tissue. The detailed visual representation of the joint therefore facilitates guidance of the surgeon during arthroscopy.

In an embodiment, the first learning model was previously trained with a second set of monocular intraoperative two-dimensional training images and a set of associated ground truths, said ground truths being distances obtained using pairs of images acquired at different times using an imaging device, said training imaging device, and information relating to positions and orientations of said training imaging device.

For example, the training imaging device may be identical to the imaging device 1 or have similar technical specificities.

In an embodiment, the first learning model was previously trained with a third training set comprising a plurality of training subsets acquired on a plurality of cadavers by the training imaging device, each training subset comprising:

a monocular two-dimensional image, comprising at least a portion of interest of the cadaveric joint; and the associated ground truth, said associated ground truth being a depth map representative of the distance between the training imaging device and the at least one portion of interest of the cadaveric joint represented in the monocular two-dimensional image.

For example, the associated ground truth can be obtained by following the following steps:

positioning on a first bone of the joint a first marker, the first marker making it possible to obtain information relating to a position and an orientation of the first bone of the joint;

positioning on a second bone of the joint a second marker, the second marker making it possible to obtain information relating to a position and an orientation of the second bone of the joint;

positioning on the training imaging device a third marker, the third marker making it possible to obtain information relating to a position and an orientation of the training imaging device;

positioning a fourth marker on a feeler, the fourth marker making it possible to obtain information relating to a position and an orientation of the feeler;

using the feeler, performing bone morphing for each of the bones on which a marker has been positioned, to obtain distance data relating to the portion of interest of the joint; these distance data express the distance between different palpated points (i.e. points scanned during bone morphing) of the joint;

(optionally) performing a reset (e.g. 3D/3D reset) between all the various palpated points and a three-dimensional model of the bones (first bone and second bone) obtained from the bones stripped by a surface scanner, so as to obtain a reset 3D model of the object in the image; this step in fact makes it possible to obtain distance data for points that have not been palpated; this optional step makes it possible to complete the cloud of palpated points with all the points that have not been palpated, calculating the distances between said reset 3D model (i.e., reset cloud of points associated with 3D model, e.g. file in STL format) and the training imaging device from the information relating to a position and an orientation of the various markers and the distance data relating to the portion of interest of the joint obtained by bone morphing;

deducing said associated ground truth in which each pixel is associated with a distance between the training imaging device and the reset 3D model representing the portion of interest of the joint.

For example, for the ground truth of each training subset, the portion of interest of the joint may correspond to a cadaveric joint or to an artificial model of the joint of the patient.

In an embodiment illustrated in FIG. 3, the training phase 200 comprises three training subphases E201, E202 and E203. These three sub-phases can be executed in any order. Alternatively, the training phase 200 may comprise only one or two training subphases among the subphases E201, E202 and E203.

During a first training subphase E201, the artificial neural network is trained on a database $B_1$ containing a first set of monocular intraoperative two-dimensional training images, comprising the joint of the patient, and a set of associated ground truths. A complete three-dimensional model of the joint of the patient, described below, obtained preoperatively from MRI images comprising the joint.

For example, the preoperative three-dimensional model is obtained from preoperative magnetic resonance imaging (MRI) data. The data comprise various slices of the joint of the patient. "Slice" means a two-dimensional image. The various slices are slices in planes parallel respectively to the sagittal, axial and coronal planes as defined in the magnetic resonance imaging field. The MRI technique can be two-dimensional, i.e. based on sequential acquisition triplets, or three-dimensional, i.e. based on volume acquisitions. Alternatively, other techniques allowing to acquire several slices of zones of interest can be used, such as for example computational axial tomography.

The magnetic resonance imaging technique presents the advantage of providing data relating to anatomical structures that are not accessible by techniques such as radiography. Thus, the preoperative three-dimensional model can comprise, for example, apart from a representation of the bone contours of the femur, of the tibia, of the patella and of the head of the fibula, a representation of the cartilaginous contours of the femur and of the tibia, a complete or partial representation of the anterior cruciate ligament, of the posterior cruciate ligament, of the external lateral ligament, of the internal lateral ligament and of the femoropatellar ligament.

The database $B_1$ is generated using 3D imaging software. For example, the Blender software can be used. The preoperative three-dimensional model is opened using the 3D imaging software. For each image in the images of the first set of monocular intraoperative two-dimensional training images, a virtual imaging device integrated with the 3D imaging software and reproducing the same optical properties as a so-called training imaging system is positioned in order to obtain a view of the preoperative three-dimensional model superimposable on the image in question. For the corresponding position of the virtual imaging system, it is then possible to calculate an associated depth map. The training imaging device is identical to the imaging device 1, which will be used intraoperatively. Thus, the principle of generating the database $B_1$ relies on the association of the preoperative three-dimensional model, and therefore of a depth map, with each intraoperative two-dimensional image in the first set.

More specifically, a monocular intraoperative two-dimensional training image in the first set is associated with a ground truth representing a distance map corresponding to the distances between the imaging device 1 and each pixel of the intraoperative arthroscopic image, assuming that these distances are equivalent to the distances between the virtual imaging device and each pixel of the three-dimensional preoperative model filmed virtually using the 3D imaging software at the same angle of view as the monocular intraoperative two-dimensional image and superimposable thereon. These manipulations make it possible to generate the database $B_1$ making it possible to perform the training subphase 201.

Following the first training subphase 201, a second training subphase 202 is performed on a second database $B_2$ containing a second set of monocular intraoperative two-dimensional training images and a second set of associated ground truths.

The second database $B_2$ is generated by intraoperatively acquiring, by means of a training imaging device, similar to the imaging device 1, images at two different times t and $t_1$ and with different viewpoints. The training imaging device is tracked during these acquisitions using a training tracking device, similar to the tracking device 3, so as to know the position in the space of the training imaging device at time t and time $t_1$. The training imaging device may coincide with the imaging device 1. The training tracking device may coincide with the tracking device 3. Following the acquisitions, a "stereo multiview" algorithm is implemented so as to make it possible to identify the same remarkable points on the image at the time t and the image at time $t_1$. Thus, the algorithm marks a remarkable point $P_i$ on the image at time t and the same remarkable point $P_i$ on the image at time $t_1$. Knowing the positions in space of the training imaging device at times t and $t_1$, the distance between the training imaging device and each remarkable point $P_i$ can be calculated. This Multiview Stereo method thus makes it possible to generate the second database $B_2$ for the training subphase 202.

Following the second training subphase 202, a third training subphase 203 is performed on a third database $B_3$ containing a third set of monocular intraoperative two-dimensional training images and a third set of associated ground truths. The images in the third set are two-dimensional images of cadaveric joints, referred to as cadaveric images, acquired with an imaging device referred to as a training device similar to the imaging device 1 used during the operation.

The ground truths of the third database $B_3$ are distance maps corresponding to the distances between the training device and the points of the cadaveric image captured by the training device. Acquisition of ground truths is performed in several steps, using a training tracking device, and markers positioned on various instruments but also on various anatomical structures. The tracking device may be a system of binocular infrared cameras of the NDI camera type or several calibrated infrared cameras of the Optitrack camera type. The markers can be made using rigid bodies equipped with at least 3 reflective spheres. These systems are typically used in computer-assisted surgery and enable efficient tracking that can offer a positioning accuracy of less than 0.5 mm.

More specifically, in a first step a), a first marker is placed and fixed in the femoral bone (femur) of the cadaveric joint, and a second marker is placed and fixed in the tibial bone (tibia). The first marker and the second marker will be used to know the position in the femur and tibia space in real time.

In a second step b), a marker is placed and secured on the training imaging device, which will be used to know in real time the position in the space of the training imaging device.

In a third step c), a marker is placed and secured on a feeler, which will be used to know in real time the position in the space of the latter.

In a fourth step d), points on the femur and on the tibia are palpated by the feeler. The position of the feeler when in contact with the femur is recorded in real time to record a point cloud located on the surface of the femur. All the palpated points constitute a cloud of points for which the distance between palpated point and training imaging device is known thanks to the training tracking device and the markers. Similarly, a cloud of points corresponding to the surface of the tibia is generated, for which the distance between palpated point and training imaging device is known.

For example, the cloud of points corresponding to the femur is generated, wherein the position of the points in space relative to the femoral marker is known. Similarly, the cloud of points corresponding to the femur is generated, wearing the position of the points in the space relative to the tibial marker is known. Then the scene is filmed using the training tracker device in the absence of the feeler. Knowing the position of the training imaging device relative to the femoral marker for the femur, and knowing the position of the cloud of points relative to the femoral marker, the distance between the training imaging device and the cloud of points is known.

Thus, during the surgery, when a monocular intraoperative two-dimensional image is received from the imaging device at a current time $t_c$, the artificial neural network, previously trained during step 200, outputs a corresponding depth map.

Optionally, the depth map associated with a monocular intraoperative two-dimensional image obtained in step E2 can be pre-processed. Indeed, the latter may contain outliers. Thus, during an intermediate step following the first calculation step E2 but preceding the second calculation step E3, a filtering can be performed on the depth map obtained in step E2. Algorithms such as RANSAC or Branch&Bound algorithms, algorithms for learning via clustering, can be used.

In other words, optionally, an intermediate step of filtering outlier data of the depth maps is implemented. Data filtering can be performed using a Kalman filter (e.g. an extended EKF filter: Extended Kalman Filter or UKF filter: "Unscented Kalman Filter") or a Monte Carlo filter (i.e. particle filter).

For example, the intermediate step of filtering outlier data may consist in filtering the depth map associated with said current time $t_c$ and the depth map associated with said previous time $t_c-\Delta t$ by comparing these depth maps. $\Delta t$ is the time difference between the acquisition of the monocular intraoperative two-dimensional image obtained at time $t_c-\Delta t$ and the monocular intraoperative two-dimensional image obtained at time $t_c$.

This intermediate step of filtering data may further comprise an evaluation of the quality of the calculated depth maps, for example by comparing several calculated depth maps and on the basis of the result of this comparison (e.g., two maps of too dissimilar depths may be associated with a poor quality of one or two depth maps). If the quality of one or two maps is not considered sufficient, the map(s) can be recalculated using the first previously trained learning model.

The second calculation step E3 will now be described in more detail.

During the second calculation step E3, the current partial three-dimensional model 8 of the joint of the patient at the time $t_c$ is calculated. The calculation uses at least one monocular intraoperative two-dimensional image obtained at and/or before the current time $t_c$, at least one depth map calculated at and/or before the current time $t_c$, information relating to a current position and orientation of the imaging device, and a complete preoperative three-dimensional model of the joint of the patient.

In particular, step E3 may comprise calculating a current partial three-dimensional model 8 of the joint of the patient associated with the current time $t_c$, on the basis of:

at least one depth map associated with the current time $t_c$ and at least one depth map associated with a previous time $t_c-\Delta t$ at the current time $t_c$, information on location of the imaging device 1, and a preoperative three-dimensional model of the joint of the patient.

In an embodiment, said information on location of the imaging device 1 comprises at least:

measured location information comprising: a first position and orientation of the imaging device 1 and a second position and orientation of the imaging device 1, being measured by the tracking device 3 respectively at said current time $t_c$ and at said previous time $t_c-\Delta t$; and calculated location information comprising: a first position and orientation of the imaging device 1 calculated on the basis of at least one monocular intraoperative two-dimensional image associated with said current time $t_c$ and a second position and orientation of the imaging device 1 calculated based on at least one monocular intraoperative two-dimensional image associated with said previous time $t_c-\Delta t$.

The measured location information may be obtained by the tracking device 3 which may be a virtual reality (VR) headset comprising at least one integrated display and/or motion sensor(s).

In an embodiment, the calculated location information is obtained by an algorithm of the "structure from motion-"type.

The time difference $\Delta t$ can be set according to several parameters. In one example, $\Delta t$ is chosen according to the amount of movement observed in the stream of monocular intraoperative two-dimensional images and/or a sampling step that governs the acquisition frequency of the stream of two-dimensional images. For example, if the amount of motion is high, i.e. the scene changes faster, you can choose to acquire more images, and therefore choose a smaller sampling step. On the other hand, if the amount of motion is low, i.e. the scene varies more slowly, you can choose to acquire fewer images, and therefore choose a larger sampling step.

The choice of the time difference $\Delta t$ can be made on the basis of a comparison between the monocular intraoperative two-dimensional images, for example by relying on a measurement of similarity/correlation between the two-dimensional images. The similarity measurement can be a direct measurement by mathematical function applied to the images or a measurement obtained by a machine learning model.

Figure 6:
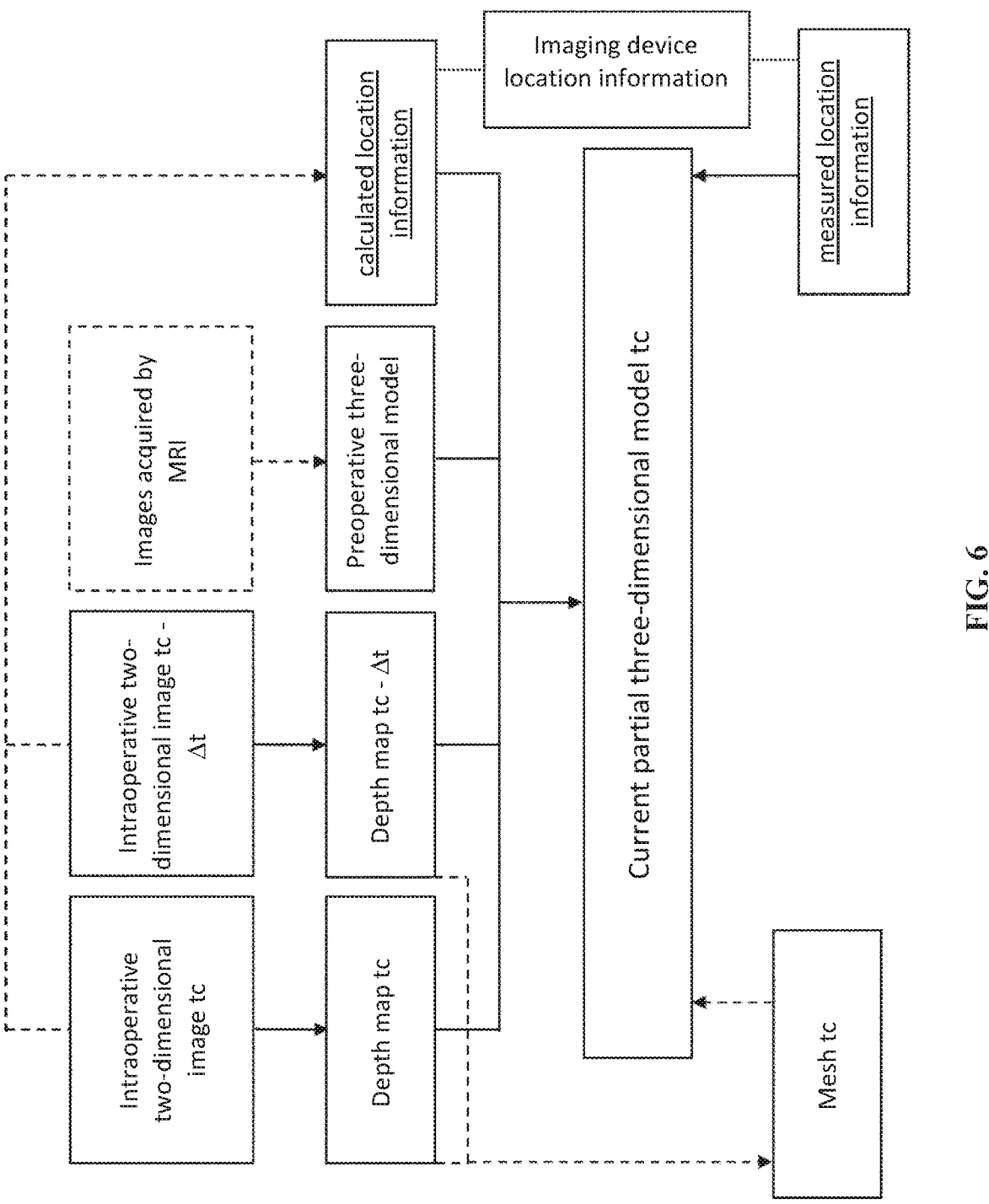
FIG. 6 is a block diagram that illustrates options for the steps of the method for modelling a joint of a patient according to one or more embodiments.

In an embodiment illustrated in FIG. 6, prior to calculating a current partial three-dimensional model 8 of the joint, the method 100 further comprises: obtaining a prediction of a mesh associated with the current time $t_c$, said mesh being representative of at least a portion of interest of the joint, using a second trained model configured to receive as input a depth map associated with said current time $t_c$ and a depth map associated with said previous time $t_c-\Delta t$. For example, the mesh associated with the current time $t_c$ may be obtained by a triangulation algorithm, a subdivision algorithm, or through a triangulation algorithm of the SLAM type.

In an embodiment, the calculation of a current partial three-dimensional model 8 is performed by a graphical neural network (i.e. GNN for "Graph/Graphical Neural Network") receiving as input the measured location information, the calculated location information, the prediction of a mesh and the preoperative three-dimensional model of the joint of the patient. One advantage of the graphical neural network is the possibility of continuously updating (i.e., in real time) the mesh associated with the current time $t_c$ and consequently the current partial three-dimensional model 8 of the joint of the patient associated with the current time $t_c$. In other words, the graphical neural network can allow servo-control of the prediction of the mesh associated with the current time $t_c$ and the calculation of the current partial three-dimensional model 8 by taking into account at least: a prediction of the mesh associated with the current time $t_c$ or a preceding time $t_c-\Delta t$, the location information calculated at the current time $t_c$ or a preceding time $t_c-\Delta t$, the measured information on location of the imaging device 1, and a preoperative three-dimensional model of the joint of the patient.

For example, the graphical neural network can compare:

the calculated location information with the measured location information; and the prediction of the mesh (calculated at the current time $t_c$) with the preoperative three-dimensional model of the joint of the patient (measured);

the calculated location information with the preoperative three-dimensional model of the joint of the patient (measured);

the measured location information with the mesh prediction (calculated at the current time $t_c$);

and based on this comparison, the graphical neural network can assign a confidence score (e.g., decimal value between 0 and 1, percentage) to the measurements (i.e., the measured location information and the preoperative three-dimensional model of the joint of the patient) and calculations (i.e., the calculated location information and the mesh prediction) according to predefined rules. For example, predefined rules can be based on a calculation of errors.

For example, the calculation of step E3 may use all of the monocular intraoperative two-dimensional images acquired by the imaging device 1 over a period [t1, $t_c$], with t1 a time preceding the current time $t_c$ (i.e., previous time $t_c-\Delta t$) and all of the corresponding depth maps. In yet another example, a sub-sampled set of monocular intraoperative two-dimensional images acquired by the imaging device 1 over a period [t1, $t_c$] may be used for the calculation. For example, one monocular intraoperative two-dimensional image out of N may be used, with N an integer between 2 and 30. N may vary according to the speed of movement of the imaging device 1 in order to obtain the best compromise between calculation accuracy and processing time. Furthermore, N may also vary depending on an amount of movement observed in the stream of monocular intraoperative two-dimensional images.

In one example, an algorithm of the SLAM type (Simultaneous Localization and Mapping) is used to calculate the current partial three-dimensional model 8. Algorithms of the SLAM type allow, from the use of two-dimensional images acquired by an image sensor, and from the position in space of the image sensor, to produce, by means of predictions of depth maps associated with the two-dimensional images, a three-dimensional mapping of the scene observed in the two-dimensional images. The three-dimensional mapping obtained can then be registered in a reference frame associated with the image sensor that acquires the two-dimensional images. Moreover, this three-dimensional mapping is dynamic. In other words, it can be obtained in real time, as the image sensor acquires the two-dimensional images of the scene.

A combination of a Structure from Motion (SfM) type algorithm and a SLAM type architecture, based on graph theory, can be used, as previously indicated. The SLAM-type architecture makes it possible, by inverted mechanism, to predict the position and orientation of the camera from the analysis of two-dimensional images comprising the joint at different times. For example, an architecture selected from DefSLAM, ORBSLAM or EKF-SLAM may for example be used.

In this case, the algorithm of the SfM type (Structure From Motion) makes it possible to obtain the calculated location information that will be used for the generation of a three-dimensional model of the observed joint from two-dimensional images captured at different times, and thus in also different positions and orientations. For example, a Multi View Stereo (MVS) type architecture can be used as the architecture for the first learning model.

As described previously, a graph matching solution can be used by using characteristic points as nodes to enable the construction of a Graph Neural Network (GNN). For example, a Bayesian model or a Kalmann model as defined by graph theory may be used. The use of self-awareness and cross-awareness layers via transformers enables the exchange of overall visual and geometric messages between nodes. Despite the possible movement of the observed anatomy over time, the exploitation of known extrinsic data, such as the camera position (i.e., information on location of the imaging device 1) and the preoperative three-dimensional model of the joint of the patient allows a reduction in quadratic complexity and convergence of the system for the establishment of a partial three-dimensional model of the observed joint.

Other architectures that can implement a SLAM algorithm type can be used, in particular LSTM networks, "Non Rigid Structure from Motion" architectures, Shape from Template architectures, DefSLAM, ORBSLAM, MISSLAM and EKF-SLAM architectures, statistical models (graph theory, Bayesian model, Kalmann model).

In other embodiments, alternatively to using an algorithm of the SLAM type, a reinforcement learning method may be used to calculate the current partial three-dimensional model 8 of the joint of the patient at the current time $t_c$.

In other words, in an alternative embodiment, the calculation of a current partial three-dimensional model 8 is performed by a reinforcement learning model being configured to receive as input the depth map associated with the current time $t_c$, the measured location information, and the preoperative three-dimensional model of the joint of the patient. This reinforcement learning model can be used as an alternative to the graphical neural network to enable the prediction of the mesh associated with the current time $t_c$ thanks to the actions performed by a reinforcement agent taking as input the preoperative three-dimensional model of the joint of the patient, the depth map associated with the current time $t_c$ and the measured location information.

Reinforcement learning involves, for an autonomous agent, such as a robot, learning the actions to take, based on experiences, in order to optimise quantitative rewards over time. The agent is immersed in an environment and makes its decisions based on its current state. Here, the actions to be taken designate the achievement of a match between a depth map obtained in step E2 and a scene observed by the agent. The scene observed by the agent represents the environment and is a perspective view simulating the view captured by a virtual camera. The agent is trained to manipulate the complete preoperative three-dimensional model of the joint of the patient so as to match a monocular intraoperative two-dimensional image obtained at a current time $t_c$ and the perspective view simulating the view captured by the virtual camera. The manipulation of the preoperative three-dimensional model is performed by means of six degrees of freedom, i.e. three translation data and three rotation data of the model. At the end of training of the reinforcement learning model, an agent is obtained capable of manipulating the preoperative three-dimensional model (by a series of translation and rotation actions) and estimating its three-dimensional position relative to the position of the virtual camera.

In one example, the training of the reinforcement learning model is performed with a nested policy of the type Nested Policy Fitted A-Iteration. The reinforcement learning model receives as input the stream of monocular intraoperative two-dimensional images, and the at least one depth map obtained in step E2. The constraints considered are then the position of the imaging device included in the information regarding the current position and orientation of the imaging device and the preoperative three-dimensional model.

The environment is thus a field of view of the preoperative three-dimensional model captured by the virtual camera. The position and orientation of the virtual camera are fixed. With the reinforcement learning model, it is sought to optimise a depth map corresponding to the field of view of the environment and the size of the size of the monocular intraoperative two-dimensional images, with the at least one depth map obtained in step E2 as the target.

In one example, during the surgery, the imaging device 1 is initially positioned at a characteristic position making it possible to optimise the calculations with the reinforcement learning model and to reduce the calculation time. An example of a characteristic position is to display the femoral trochlea and the foot of the anterolateral cruciate ligament.

For example, the training of the reinforcement learning model is carried out via a training policy called Clipped Double Q-Learning (CDQ), aimed at jointly minimising a first and second cost function.

Thus, for example, the first cost function is representative of the distance between the depth of the pixels of the depth map that is sought to be optimised and the depth of the at least one depth map obtained in step E2. For example, the second cost function is representative of the costs charged by the nested policy, in particular the constraints related to the intraoperative three-dimensional model and the movement of the imaging device 1. The constraints related to the intraoperative three-dimensional model may be related to the intra-articular nature of the procedure, which limits the actions of the agent in space. The actions of the agent (translations and rotations of the preoperative three-dimensional model) may also be limited by the actual movement of the imaging device 1. Indeed, the information delivered by the tracking device 3 can be used to make assumptions about the correct or incorrect nature of the actions performed by the agent (e.g., a movement too far, an incorrect direction, an incorrect direction of rotation). A Markovian decision process can be used for this purpose.

The training of the reinforcement learning model can be carried out in several steps. In a first step of training, an arthroscopic flow resulting from a surgical procedure of a patient where a preoperative three-dimensional model of the joint of interest, a so-called training model, is known from MRI images may be used. The arthroscopic flow is successively read and then stopped on a given image. A prediction is then made by the agent. An operator then manually positions the training model viewed by a virtual camera, so that the field of view of the virtual camera is recalibrated to the given image on which the arthroscopic flow has been stopped. By backpropagation, the weights and biases of the reinforcement learning model are adjusted so as to take into account the result of the recalibration by the operator. This sequence of sub-steps is repeated as many times as the arthroscopic flow is read and stopped. In a later training step, the ground truths (which are depth maps) from the third database $B_3$ mentioned above can be used. During this subsequent training step, an algorithm automatically rescales the three-dimensional training model to structures identified in the ground truths of the third database $B_3$.

Models different from the examples presented above may be used, such as the following solutions: DDPG, PPG, TRPO, REAR, SAC, DQ-AC, DDQN-AC, DDPG (Deep Deterministic Policy Gradient Algorithm), Random Compression Rehearsal.

When an action is performed by the agent, the scene, in other words the environment, is updated, as well as the current partial three-dimensional model 8 of the joint of the patient of each action iteration.

Thus, from monocular intraoperative two-dimensional images containing the joint of the patient and obtained up to the current time $t_c$, and associated depth maps calculated in step E2, a current partial three-dimensional model 8 of the joint of the patient is obtained. This model is located in a reference frame associated with the imaging device 1, which acquires the monocular intraoperative two-dimensional images.

Once the current partial three-dimensional model 8 has been calculated, it is recalibrated on a preoperative three-dimensional model of the joint of the patient. For example, this is a preoperative three-dimensional model obtained from preoperative images of the joint of the patient.

In one example, the preoperative three-dimensional model of the joint of the patient contains theoretical positions of the bone tunnel(s) to be made in the joint of the patient. These theoretical positions were, for example, preplanned when planning the surgery. Thus, following the recalibration, the current partial three-dimensional model can be superimposed on these theoretical positions. Furthermore, the preoperative three-dimensional model may contain a representation of anatomical structures.

Advantageously, the surgeon performing the operation can view on a display device 12, on the one hand the superposition of the current partial three-dimensional model at a time t on the theoretical positions of the bone tunnel(s) to be produced in the joint and on the representation of anatomical structures of interest, and at the same time the position of this superposition relative to the position of the imaging device and that of the surgical piercing instrument, or more precisely the tip of the surgical piercing instrument. In this way, the surgeon can modify its position so as, on the one hand, to be in accordance with the theoretical positions of the bone tunnel(s) to be made, and, on the other hand, to manipulate it in full knowledge of its location relative to anatomical structures that could be areas to avoid or to preserve.

The calculation of the current partial three-dimensional model 8 is performed in real time. Thus, the latter can also be displayed in real time on the display device 12, so as to allow immediate feedback to the surgeon.

Figure 4:
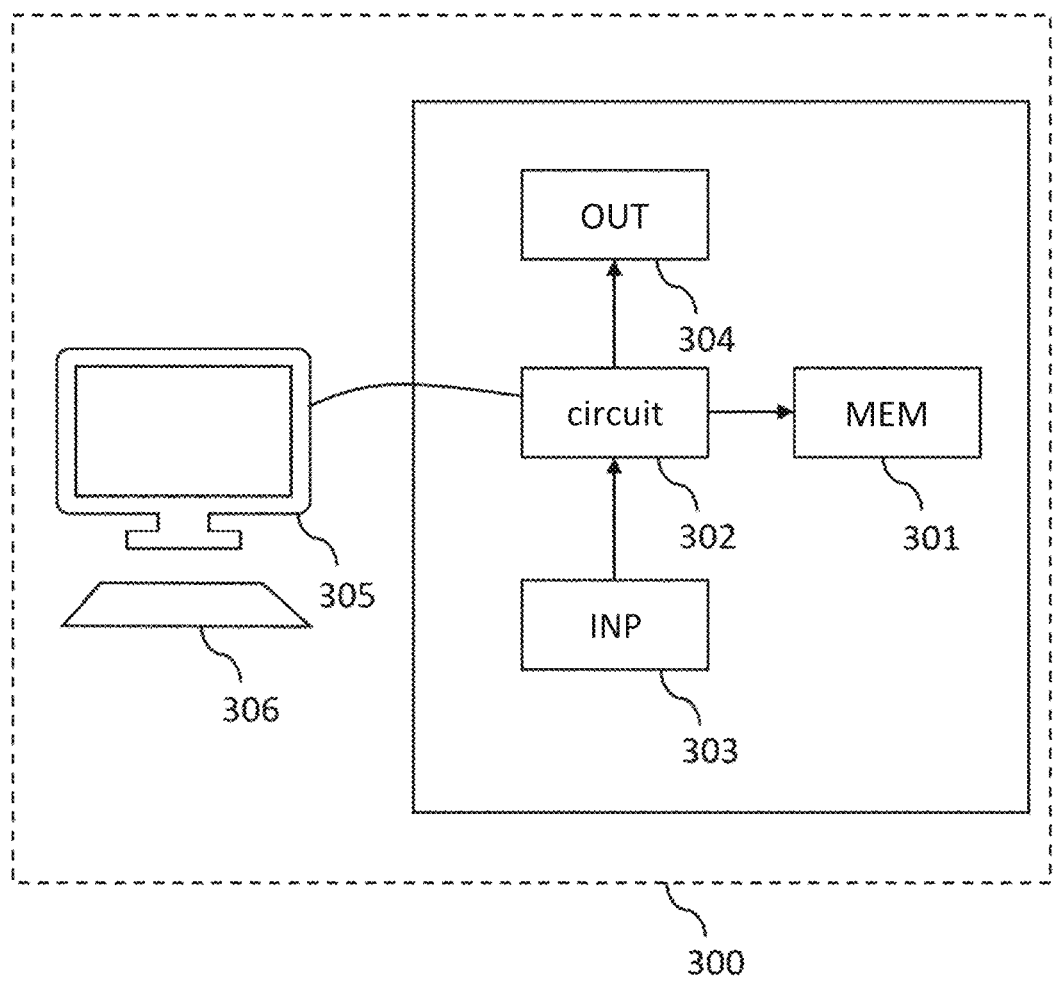
FIG. 4 illustrates a device for implementing a method for modelling a joint of a patient according to one or more embodiments.

FIG. 4 illustrates a device 300 for implementing computer-implemented methods for modelling a joint of a patient for real-time assistance in making at least one bone tunnel by arthroscopy according to one or more embodiments.

The device 300 may comprise a memory 301 for storing instructions for implementing steps of the methods for modelling a joint of a patient to perform all or some of the steps of the methods described above.

The device 300 further comprises a control circuit 302, an input interface 303 for receiving data, including training data of the learning model and/or the monocular intraoperative two-dimensional images acquired by the imaging device 2, and an output interface 304 for providing output data, such as parameters of the previously trained learning model or the current partial three-dimensional model, in real time.

In one or more embodiments, to enable easy interaction with a user, the device 300 may be in the form of a computer including a screen 305 and a keyboard 306. The device 300 may be a mobile terminal, a computer, a network of computers, an electronic component, or another apparatus comprising a processor operatively coupled to a memory, as well as, according to the chosen embodiment, a data storage unit, and other associated hardware such as a network interface and a media reader for reading a removable storage medium and writing on such a medium. The removable storage medium can be, for example, a compact disk (CD), a video/digital versatile disk (DVD), a flash disk, a USB stick, etc. Depending on the embodiment, the memory, data storage unit, or removable storage medium contains instructions that, when executed by the control circuit 302, cause this control circuit 302 to control the input interface 303, output interface 304, and memory 301.

The control circuit 302 may be a component implementing a processor or a computing unit to train a learning model and/or compute a current partial three-dimensional model of a joint of a patient according to the proposed method and to control the units 301, 303 and 304 of the device 300. Furthermore, the device 300 may be implemented in the form of software (software or firmware), in which case it takes the form of a program executable by a processor, corresponding for example to an application downloadable and executable on equipment of the smart phone or tablet type, as described above, or in hardware form (or "hardware"), such as an application-specific integrated circuit (ASIC), a "System On Chip", or SOC), or in the form of a combination of hardware and software elements, for example a software program intended to be loaded and executed on a component of the FPGA (Field Programmable Gate Array) type. SOCs are embedded systems that integrate all the components of an electronic system in a single chip. An ASIC (Application Specific Integrated Circuit) is a specialised electronic circuit that groups together customised functionalities for a given application. ASICs are generally configured during manufacture and can only be simulated by the user. Programmable logic circuits of the FPGA type have electronic circuits that can be reconfigured by the user. The device 300 may also use hybrid architectures, for example architectures based on a CPU+FPGA, a GPU (standing for "Graphics Processing Unit") or an MPPA (standing for "Multi-Purpose Processor Array").

Furthermore, the block diagram shown in FIG. 1 is a typical example of a program in which certain instructions can be performed by the device described. As such, FIG. 1 may correspond to the flowchart of the general algorithm of a computer program in a particular embodiment.

The invention claimed is:

1. A computer-implemented method for modelling a joint of a patient for real-time assistance in creating at least one bone tunnel by arthroscopy or during open surgery in said joint, comprising:

receiving at least one of a stream of monocular or binocular intraoperative two-dimensional images obtained using an imaging device, each of the monocular or binocular intraoperative two-dimensional images being obtained at a time t and comprising at least a portion of interest of the joint;

for each monocular or binocular intraoperative two-dimensional image, calculating a depth map associated with the time t, by implementing a first previously trained learning model, said first learning model configured to receive as input at least said monocular or binocular intraoperative two-dimensional image obtained at the time t;

filtering outlier data from at least one depth map associated with a current time tc and at least one depth map associated with a previous moment ($t_c$–$\Delta$t), by comparing said depth maps; and calculating a current partial three-dimensional model of the joint of the patient associated with the current time tc, on the basis of the at least one filtered depth map associated with the current time tc and the at least one filtered depth map associated with the previous time ($t_c$–$\Delta$t), and location information of the imaging device.

2. The method according to claim 1, wherein said location information on the imaging device comprises at least:

measured location information comprising: a first position and orientation of the imaging device and a second position and orientation of the imaging device, measured by a tracking device respectively at said current time tc and at said previous time ($t_c$–$\Delta$t); and, calculated location information comprising: a first position and orientation of the imaging device calculated on the basis of at least one monocular or binocular intraoperative two-dimensional image associated with said current time tc and a second position and orientation of the imaging device calculated on the basis of at least one monocular or binocular intraoperative two-dimensional image associated with said previous time ($t_c$–$\Delta$t).

3. The method of claim 2, wherein said calculated location information is obtained by an algorithm of the "Structure from motion" type.

4. The method of claim 2, wherein calculating a current partial three-dimensional model is performed by a graphical neural network receiving as input at least said measured location information, said calculated location information, and a preoperative three-dimensional model of the joint of the patient.

5. The method of claim 2, wherein calculating a partial three-dimensional model of the joint of the patient is performed by a reinforcement learning model configured to receive as input at least said measured location information, said calculated location information, and a preoperative three-dimensional model of the joint of the patient.

6. A non-transitory computer-readable recording medium comprising instructions which, when they are executed by a computer, cause the computer to implement the method of claim 2.

7. The method of claim 1, wherein the first previously trained learning model is an artificial neural network.

8. The method of claim 1, wherein the first learning model has been previously trained with a first set of monocular or binocular intraoperative two-dimensional training images and a set of associated ground truths, wherein said ground truths are distances between a virtual imaging device and at least one object included in the first set of monocular or binocular intraoperative two-dimensional training images, wherein each of the monocular or binocular intraoperative two-dimensional training images of the first set of monocular or binocular intraoperative two-dimensional training images represents a virtual image obtained with said virtual imaging device comprising in its field of view said at least one object, the object being a preoperative three-dimensional model of the joint of the patient.

9. The method of claim 8, wherein the preoperative three-dimensional model was obtained from two-dimensional medical images, said two-dimensional medical images comprising at least said portion of interest of the joint.

10. The method of claim 8, wherein said preoperative three-dimensional model of the joint of the patient is obtained from images acquired by "Magnetic Resonance Imaging", said acquired images comprising at least said portion of interest of the joint.

11. The method of claim 1, wherein the first learning model has been previously trained with a second set of monocular or binocular intraoperative two-dimensional training images and a set of associated ground truths, wherein said ground truths are distances obtained using pairs of images acquired at different times using a training imaging device and information relating to positions and orientations of said training imaging device.

12. The method of claim 1, wherein the first learning model has been previously trained with a third training set comprising a plurality of training subsets acquired on a plurality of cadavers by a training imaging device, each training subset comprising:

a monocular or binocular two-dimensional image, comprising at least a portion of interest of the cadaveric joint; and, an associated ground truth, wherein said associated ground truth is a depth map representative of the distance between the training imaging device and said at least one portion of interest of the cadaveric joint represented in the monocular or binocular two-dimensional image.

13. The method of claim 1, wherein calculating the current partial three-dimensional model of the joint of the patient is further based on a preoperative three-dimensional model of the joint of the patient.

14. A non-transitory computer-readable recording medium comprising instructions which, when they are executed by a computer, cause the computer to implement the method of claim 1.

15. A device for modelling a joint of a patient for real-time assistance in creating at least one bone tunnel by arthroscopy or during open surgery in said joint, said device comprising:

at least one input configured to receive at least one of a stream of monocular or binocular intraoperative two-dimensional images obtained using an imaging device, each of the monocular or binocular intraoperative two-dimensional images being obtained at a time t and comprising at least a portion of interest of the joint;

at least one processor configured to:

for each monocular or binocular intraoperative two-dimensional image, calculate a depth map associated with the time t, by implementing a first previously trained learning model, said first learning model being configured to receive as input at least said monocular or binocular intraoperative two-dimensional image obtained at the time t;

filtering outlier data from at least one depth map associated with a current time tc and at least one depth map associated with a previous moment ($t_c$–$\Delta$t) by comparing said depth maps; and calculating a current partial three-dimensional model of the joint of the patient associated with the current time tc, on the basis of the at least one filtered depth map associated with the current time tc and the at least one filtered depth map associated with the previous time ($t_c$–$\Delta$t), and location information of the imaging device; and at least one output configured to provide said current partial three-dimensional model of the joint of the patient associated with the current time tc.

16. A computer-implemented method for modelling a joint of a patient for real- time assistance in creating at least one bone tunnel by arthroscopy or during open surgery in said joint, comprising:

receiving at least one of a stream of monocular or binocular intraoperative two- dimensional images obtained using an imaging device, each of the monocular or binocular intraoperative two-dimensional images being obtained at a time t and comprising at least a portion of interest of the joint;

for each monocular or binocular intraoperative two-dimensional image, calculating a depth map associated with the time t, by implementing a first previously trained learning model, said first learning model configured to receive as input at least said monocular or binocular intraoperative two-dimensional image obtained at the time t;

filtering outlier data from at least one depth map associated with a current time tc and at least one depth map associated with a previous moment ($t_c$–$\Delta$t) by comparing said depth maps;

generating, based at least in part on the at least one filtered depth map associated with said current time tc and the at least one filtered depth map associated with said previous moment ($t_c$–$\Delta$t), at least one prediction of a mesh associated with the current time tc, wherein said mesh is representative of at least a portion of interest of the joint; and calculating a current partial three-dimensional model of the joint of the patient associated with the current time tc, on the basis of the at least one filtered depth map associated with the current time tc and the at least one filtered depth map associated with the previous time ($t_c$–$\Delta$t), and location information of the imaging device, and the at least one prediction of a mesh associated with the current time tc.

17. The method according to claim 16, wherein said location information on the imaging device comprises at least:

measured location information comprising: a first position and orientation of the imaging device and a second position and orientation of the imaging device, measured by a tracking device respectively at said current time tc and at said previous time ($t_c$–$\Delta$t); and, calculated location information comprising: a first position and orientation of the imaging device calculated on the basis of at least one monocular or binocular intraoperative two- dimensional image associated with said current time tc and a second position and orientation of the imaging device calculated on the basis of at least one monocular or binocular intraoperative two-dimensional image associated with said previous time ($t_c-\Delta t$).

18. The method of claim 17, wherein calculating a current partial three-dimensional model is performed by a graphical neural network receiving as input at least said measured location information, said calculated location information, said prediction of a mesh and a preoperative three-dimensional model of the joint of the patient.

19. The method of claim 17, wherein calculating a partial three-dimensional model of the joint of the patient is performed by a reinforcement learning model configured to receive as input at least said measured location information, said calculated location information, said prediction of a mesh and a preoperative three-dimensional model of the joint of the patient.

20. The method of claim 16, wherein calculating the current partial three- dimensional model of the joint of the patient is further based on a preoperative three-dimensional model of the joint of the patient.

* * * * *